United States Patent [19]

Tyers

[11] Patent Number: 4,948,803

[45] Date of Patent: Aug. 14, 1990

[54] MEDICAMENTS FOR TREATMENT ON PREVENTION OF WITHDRAWAL SYNDROME

[75] Inventor: Michael B. Tyers, Welwyn, England

[73] Assignee: Glaxo Group Limited, London, England

[21] Appl. No.: 246,550

[22] PCT Filed: Nov. 20, 1987

[86] PCT No.: PCT/GB87/00826

§ 371 Date: Sep. 9, 1988

§ 102(e) Date: Sep. 9, 1988

[87] PCT Pub. No.: WO88/03801

PCT Pub. Date: Jun. 2, 1988

[30] Foreign Application Priority Data

| Nov. 21, 1986 [GB] | United Kingdom | 8627909 |
| Nov. 21, 1986 [GB] | United Kingdom | 8627883 |
| Nov. 21, 1986 [GB] | United Kingdom | 8627881 |
| Dec. 17, 1986 [GB] | United Kingdom | 8630083 |
| Mar. 25, 1987 [GB] | United Kingdom | 8707177 |

[51] Int. Cl.$^5$ .................................. A61K 31/415
[52] U.S. Cl. ................................ 514/397; 514/810
[58] Field of Search ........................... 514/397, 810

[56] References Cited

U.S. PATENT DOCUMENTS 4,808,581 2/1989 Oxford et al. .................. 514/397
4,847,281 7/1989 Tyers .

FOREIGN PATENT DOCUMENTS 0200444 11/1986 European Pat. Off. .
0201165 11/1986 European Pat. Off. .
0272052 6/1988 European Pat. Off. .
2193633 2/1988 United Kingdom .
2206788 1/1989 United Kingdom .

Primary Examiner—Stanley J. Friedman
Attorney, Agent, or Firm—Bacon & Thomas

[57] ABSTRACT

The treatment of withdrawal symptoms from drugs using azabicyclo indazole-3-carboxamides.

8 Claims, No Drawings

MEDICAMENTS FOR TREATMENT ON PREVENTION OF WITHDRAWAL SYNDROME

This invention relates to a new medical use for certain chemical compounds and pharmaceutical compositions containing them. In particular it relates to the use in the treatment of subjects addicted, recovering from addiction, or liable to become addicted, to drugs or substances of abuse of compounds which act as antagonists of 5-hydroxytryptamine (5-HT) at receptors known in the art as 5-HT$_3$, 5-HT'M' or 5-HT 'M'-like' receptors. Such receptors have been described for example by Fozard et al., Eur. J. Pharmacol., 1979, 59, 195–210; Ireland, Straughan and Tyers, Br. J. Pharmacol., 1982, 75, 16P; Humphrey, Neuropharm., 1984, 23, 1503–1570; Richardson et al., Nature, 1985, 316, 126–131; and Bradley et al., Neuropharm., 1986, 25, 563–576. Receptors of this type are now designated as 5-HT$_3$ receptors.

5-HT receptors of this type are located, for example, on the terminals of afferent sensory neurones, in the isolated guinea-pig ileum preparation and are also present in the central nervous system. Compounds which act as antagonists of 5-HT at 5-HT$_3$ receptors may be identified using standard tests, for example, in vitro by measuring their inhibition of the depolarising effect of 5-HT on the rat or rabbit isolated vagus nerve, or the tachycardia produced by 5-HT in the rabbit isolated heart or the contraction produced by 5-HT in the guinea-pig isolated ileum, or in vivo by measuring their effect on the Von Bezold-Jarisch reflex (induced by 5-HT) as described, for example, in the above-mentioned references.

A variety of compounds which act as antagonists of 5-HT at 5-HT$_3$ receptors have been described in the art. The known compounds are generally azabicyclo derivatives and/or benzoic acid derivatives, or imidazole derivatives. Azabicyclo derivatives include compounds containing a bridged piperidyl group, such as a tropyl, pseudotropyl, homotropyl or quinuclidinyl group. An azabicyclo derivative preferably contains a carbocyclic or heterocyclic aromatic group linked, for example as an ester or amide, to the azabicyclic ring. The aromatic group may be for example an optionally substituted phenyl, indolyl, benzofuranyl, benzothienyl, benzisoxazolyl, indazolyl or pyrimidinyl group.

Benzoic acid derivatives which act as antagonists of 5-HT at 5-HT$_3$ receptors include benzoates and benzamides. A benzoic acid derivative may for example be an ester or an amide formed with an azabicyclic group as defined above, or formed with a piperidyl group.

Such compounds have been disclosed inter alia in published UK Patent Application Nos. 2100259, 2125398, 2131420, 2132189, 2145416, 2152049, 2153821 and 2169292, published European Patent Application Nos. 111608, 116255, 158265, 191562, 200444, 210840, 214772, 219193, 221702, 226267, 227215, 230718, 235878 and 242973, and published Australian Patent Application No. 87/67121. The compounds disclosed in published European Patent Application Nos. 13138, 67615, and 94742 are described in published European Patent Application Nos. 215545 and 220011 as antagonists of 5-HT at 5-HT$_3$ receptors.

The compounds disclosed in these specifications have been described as being of use in a variety of conditions, including migraine. However there is no disclosure in these specifications of compounds which are antagonists of 5-HT at 5-HT$_3$ receptors being of use in the treatment of drug abuse.

We have now found that compounds which act as 5-HT antagonists at 5-HT$_3$ receptors may be used in the treatment of subjects addicted, recovering from addiction, or liable to become addicted, to drugs or substances of abuse.

1,2,3,9-Tetrahydro-9-methyl-3-[(2-methylimidazol-1-yl)methyl]-4H-carbazol-4-one and its salts and solvates, which are disclosed in published UK Patent Application No. 2153821A are however excluded from the present invention. It will be appreciated that general references hereinafter to "compounds which act as antagonists of 5-HT at 5-HT$_3$ receptors" and to those compounds "disclosed in published UK Patent Application No. 2153821A" exclude 1,2,3,9-tetrahydro-9-methyl-3-[(2-methylimidazol-1-yl)methyl]-4H-carbazol-4-one and its salts and solvates.

Repeated administration to a subject of certain drugs such as opiates (e.g. morphine), cocaine or benzodiazepines (e.g. diazepam, chlordiazepoxide or lorazepam), or substances of abuse such as alcohol or nicotine (e.g. smoking) can lead to physical and/or psychological dependence upon that drug or substance. When the drug or substance of abuse is withdrawn from a dependent subject, the subject develops certain symptoms, such as aggressive behaviour, agitation and intense craving for the drug or substance of abuse. These symptoms may be collectively described as a withdrawal or abstinence syndrome.

It has now been shown that administration of a compound which acts as a 5-HT antagonist at 5-HT$_3$ receptors can prevent, alleviate or reverse this withdrawal syndrome. The compounds are therefore of use for the prevention or relief of a withdrawal syndrome resulting from addiction to drugs or substances of abuse.

It has also been shown that compounds which act as 5-HT antagonists at 5-HT$_3$ receptors suppress dependence on drugs or substances of abuse. The compounds are therefore also of use in reducing the craving for a drug or substance of abuse after addiction to that drug or substance, and can therefore be used for maintainence therapy during remission from addiction to drugs or substances of abuse. The compounds may also be used for prophylactic treatment of subjects liable to become dependent on drugs or substances of abuse.

The effectiveness of compounds for use according to the present invention in the treatment of a withdrawal syndrome resulting from addiction to a drug or substance of abuse, and for the suppression of dependence on a drug or substance of abuse may be demonstrated in animals using standard tests, for example, the light/dark exploration test in mice, the rat social interaction test, a marmoset behavioural test and the 'drinkometer' alcohol consumption test in rats.

Accordingly the invention provides a method of treatment for the relief or prevention of a withdrawal syndrome resulting from addiction to a drug or substance of abuse and/or for the suppression of dependence on drugs or substances of abuse, which comprises administering to a human or animal subject an effective amount of a compound which acts as an antagonist of 5-HT at 5-HT$_3$ receptors, or a physiologically acceptable salt or solvate thereof.

Preferred compounds for use in the present invention are azabicyclo derivatives (e.g. containing a bridged piperidyl group such as a tropyl, pseudotropyl, homotropyl or quinuclidinyl group) and benzoic acid derivatives (e.g. benzoates and benzamides) which act as antagonists of 5-HT at 5-HT₃ receptors. Further preferred 5-HT₃ receptor antagonists for use in the present invention are 3-(imidazol-1-yl)methyltetrahydrocarbazolones and 3-(imidazol-4-yl)-(indol-3-yl)-1-propanones.

Particular mention may be made of the compounds which act as antagonists of 5-HT at 5-HT₃ receptors disclosed in published UK Patent Application Nos. 2100259, 2125398, 2131420, 2132189, 2145416, 2152049, 2153821 and 2169292, published European Patent Application Nos. 13138, 67615, 94742, 111608, 116255, 158265, 191562, 200444, 210840, 214772, 219193, 221702, 226267, 227215, 230718, 235878 and 242973, and published Australian Patent Application No. 87/67121.

Preferred compounds for use according to the invention are those described in published UK Patent Application Nos. 2100259, 2131794, 2132189, 2125398, 2152049 and 2153821, published European Patent Application Nos. 13138, 94742, 200444, 221702, 226267, 235878 and 242973 and published Australian Patent Application No. 87/67121.

Particularly preferred compounds for use according to the present invention are those described in published UK Patent Application Nos. 2100259 and 2125398 and published European Patent Application Nos. 94742, 200444 and 242973.

A group of compounds described in UK Specification No. 2125398 may be represented by the general formula (I):

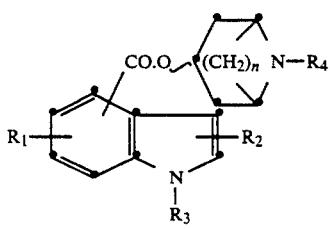

wherein R₁ and R₂ independently represent hydrogen, halogen, $C_{1-4}$ alkyl, $C_{1-4}$ alkoxy, hydroxy, amino, $C_{1-4}$ alkylamino, di($C_{1-4}$)alkylamino, mercapto or $C_{1-4}$ alkylthio;

R₃ represents hydrogen, $C_{1-4}$ alkyl, $C_{3-5}$ alkenyl, aryl or aralkyl;

R₄ represents hydrogen, $C_{1-7}$ alkyl, $C_{3-5}$ alkenyl or aralkyl;

n is 2 or 3;

the free valence is attached to either fused ring, and the azabicyclic ring is in either the exo or endo configuration; and acid addition salts and quaternary ammonium salts thereof.

In the compounds of formula (I) R₁ and R₂ may, for example, independently represent hydrogen, halogen or $C_{1-4}$ alkyl, R₃ may be, for example, hydrogen or $C_{1-4}$ alkyl and R₄ may be, for example, hydrogen, $C_{1-7}$ alkyl or aralkyl. The carbonyl group is preferably attached to the 3-position of the indole ring. The azabicyclic ring is preferably in the endo configuration.

Compounds described in UK Specification No. 2100259 may be represented by the general formula (II):

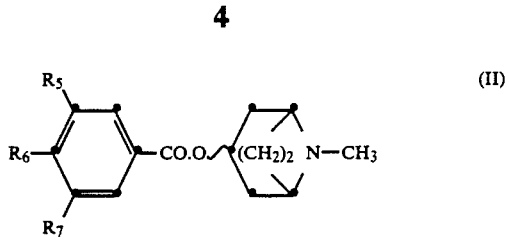

wherein R₅ represents $C_{1-4}$ alkyl, $C_{1-4}$ alkoxy, or halogen; and

R₆ and R₇ independently represent hydrogen, $C_{1-4}$ alkyl, $C_{1-4}$ alkoxy or halogen provided that R₆ is hydrogen when R₇ is hydrogen;

and pharmaceutically acceptable salts thereof.

A preferred class of compounds of formula (II) are those in which R₅ and R₇ are the same and each represents methyl, methoxy or chlorine, and R₆ represents hydrogen.

A group of compounds described in European Specification No. 94742 may be represented by the general formula (III):

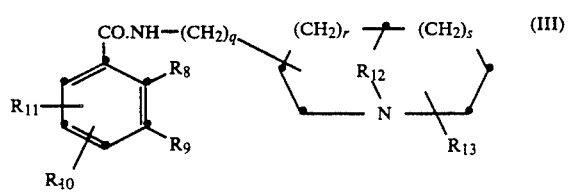

wherein R₈ represents a $C_{1-6}$ alkoxy or amino N-substituted by one or two groups selected from $C_{1-6}$ alkyl or $C_{3-8}$ cycloalkyl or optionally N-substituted by $C_{4-5}$ polymethylene;

one of R₉, R₁₀ and R₁₁ is hydrogen and the other two are independently selected from hydrogen, chloro, bromo, trifluoromethyl, hydroxy, $C_{1-6}$ alkoxy, $C_{1-6}$ alkylthio, $C_{1-6}$ alkyl and amino;

one of R₁₄ and R₁₅ represents hydrogen, $C_{1-6}$ alkyl, phenyl or phenyl$C_{1-3}$ alkyl, which phenyl moieties may be substituted by $C_{1-6}$ alkyl, $C_{1-6}$ alkoxy, $CF_3$ or halogen, and the other of R₁₂ and R₁₃ is hydrogen or $C_{1-6}$ alkyl;

q is zero or an integer from 1 to 4;

r is zero, or an integer from 1 to 3; and s is zero, 1 or 2.

Preferred compounds of formula (IV) are those wherein R₈ is methoxy, R₉ is hydrogen, R₁₀ is 4-amino, R₁₁ is 5-chloro (relative to the benzamide group), R₁₂ and R₁₃ independently represent hydrogen or $C_{1-6}$ alkyl; q is zero, r is 1 or 2 and s is zero, 1 or 2.

A group of compounds described in European Specification No. 200444 may be represented by the general formula (IV):

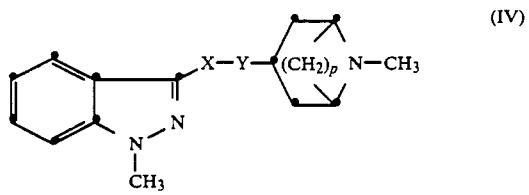

wherein X is CO and Y is NH or O;

and p is 2 or 3;

and pharmaceutically acceptable salts thereof.

Compounds described in our UK Patent Specification No. 2153821 and European Specifications Nos. 191562, 210840 and 219193 may be represented by the general formula (V):

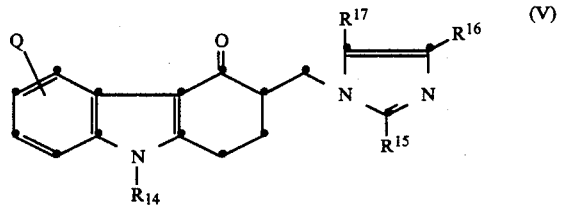

wherein $R^{14}$ represents a hydrogen atom or a group selected from $C_{1-10}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl or phenyl $C_{1-3}$ alkyl, and in the case where Q represents a hydrogen atom, $R^{14}$ may also represent $-CO_2R^{18}$, $-COR^{18}$, $-CONR^{18}R^{19}$ or $-SO_2R^{18}$ (wherein $R^{18}$ and $R^{19}$, which may be the same or different, each represents a hydrogen atom, a $C_{1-6}$ alkyl or $C_{3-7}$ cycloalkyl group, or a phenyl or phenyl $C_{1-4}$ alkyl group, in which the phenyl group is optionally substituted by one or more $C_{1-4}$ alkyl, $C_{1-4}$ alkoxy or hydroxy groups or halogen atoms, with the proviso that $R^{18}$ does not represent a hydrogen atom when $R^{14}$ represents a group $-CO_2R^{18}$ or $-SO_2R^{18}$);

one of the groups represented by $R^{15}$, $R^{16}$ and $R^{17}$ is a hydrogen atom or a $C_{1-6}$ alkyl, $C_{3-7}$ cycloalkyl, $C_{2-6}$ alkenyl, or phenyl $C_{1-3}$ alkyl group, and each of the other two groups, which may be the same or different, represents a hydrogen atom or a $C_{1-6}$ alkyl group;

Q represents a hydrogen atom or a halogen atom or a hydroxy, $C_{1-4}$ alkoxy, phenyl $C_{1-3}$ alkoxy or $C_{1-6}$ alkyl group or a group $-NR^{20}R^{21}$ or $-CONR^{20}R^{21}$ (wherein $R^{20}$ and $R^{21}$, which may be the same or different, each represents a hydrogen atom or a $C_{1-4}$ alkyl or $C_{3-4}$ alkenyl group, or together with the nitrogen atom to which they are attached form a saturated 5 to 7 membered ring);

and physiologically acceptable salts and solvates thereof.

A preferred class of compounds represented by the formula (V) for use according to the present invention is that wherein $R^{14}$ represents a hydrogen atom or a methyl, ethyl, propyl, prop-2-enyl or cyclopentyl group; $R^{16}$ represents a hydrogen atom; and either $R^{15}$ represents a methyl, ethyl, propyl or prop-2-yl group and $R^{17}$ represents a hydrogen atom or $R^{15}$ represents a hydrogen atom and $R^{17}$ represents a methyl or ethyl group; and Q represents a hydrogen atom.

A group of compounds described in European Patent Specification No. 242972 may be represented by the general formula (VI):

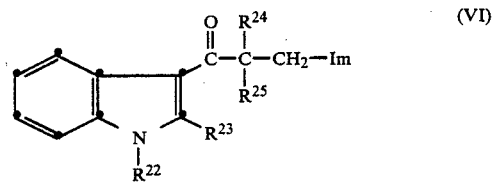

wherein Im represents an imidazolyl group of formula:

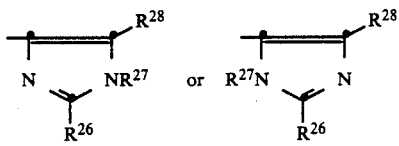

$R^{22}$ represents a hydrogen atom or a $C_{1-6}$ alkyl, $C_{3-6}$ alkenyl, $C_{3-10}$ alkynyl, $C_{3-7}$ cycloalkyl, $C_{3-7}$ cycloalkyl $C_{1-4}$ alkyl, phenyl or phenyl $C_{1-3}$ alkyl group;

$R^{23}$ represents a hydrogen atom or a $C_{1-6}$ alkyl, $C_{3-6}$ alkenyl, $C_{3-7}$ cycloalkyl, phenyl or phenyl $C_{1-3}$ alkyl group;

$R^{24}$ and $R^{25}$, which may be the same or different, each represents a hydrogen atom or a $C_{1-6}$ alkyl group;

one of the groups represented by $R^{26}$, $R^{27}$ and $R^{28}$, is a hydrogen atom or a $C_{1-6}$ alkyl, $C_{3-7}$ cycloalkyl, $C_{3-6}$ alkenyl, phenyl or phenyl $C_{1-3}$ alkyl group, and each of the other two groups, which may be the same or different, represents a hydrogen atom or a $C_{1-6}$ alkyl group;

and physiologically acceptable salts and solvates thereof.

A preferred class of compounds represented by the formula (VI) for use according to the present invention are those wherein $R^{22}$ represents a hydrogen atom or a methyl, prop-2-enyl or cyclopentyl group; $R^{23}$ represents a hydrogen atom or a methyl group; $R^{24}$ and $R^{25}$ each independently represent a hydrogen atom or a methyl group; $R^{26}$ and $R^{27}$ each represent a hydrogen atom; and $R^{28}$ represents a hydrogen atom or a $C_{1-3}$ alkyl group, most preferably methyl.

Compounds described in European Specification No. 235878 and Australian Specification No. 87/67121 may be represented by the general formulae (VII) and (VIII) respectively:

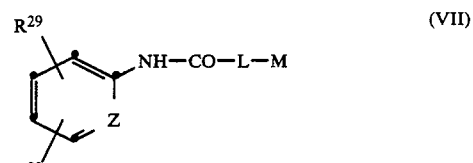

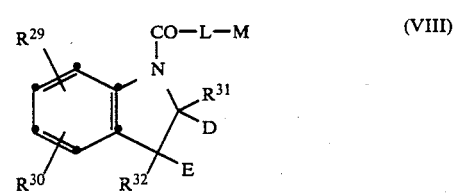

wherein L is NH or O;

$R^{29}$ and $R^{30}$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by C$_{4-5}$-polymethylene;

Z is a moiety capable of hydrogen bonding to the NH group depicted in formula (VII);

D and E are independently selected from hydrogen or C$_{1-4}$alkyl, or together are a bond;

R$^{31}$ and R$^{32}$ are independently selected from hydrogen, C$_{1-6}$ alkyl, C$_{2-6}$alkenylC$_{1-4}$alkyl, or together are C$_{2-4}$polymethylene;

M is a group of formula (a), (b) or (c):

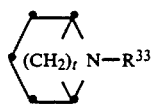 (a)

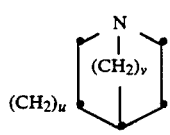 (b)

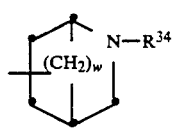 (c)

wherein t is 2 or 3;
u is 1 or 2;
v is 1 to 3;
w is 1 to 3;
and R$^{33}$ or R$^{34}$ is C$_{1-7}$alkyl, C$_{3-8}$cycloalkyl, C$_{3-8}$cycloalkylC$_{1-2}$alkyl or C$_{2-7}$alkenylC$_{1-4}$alkenyl;

and pharmaceutically acceptable salts thereof.

Preferably L is NH; R$^{29}$ is often hydrogen and R$^{30}$ is hydrogen or a 4-substituent such as halo or methoxy; Z is preferably C—OCH$_3$, C—OC$_2$H$_5$, C—OC$_3$H$_7$, C—CO$_2$CH$_3$, C—CO$_2$C$_2$H$_5$ or SO$_2$N(CH$_3$)$_2$; often D and E are both hydrogen; often R$^{31}$ and R$^{32}$ are both hydrogen; preferably t is 2 or 3 and u, v and w are 1 or 2; and R$^{33}$/R$^{34}$ is preferably methyl or ethyl, most preferably methyl.

A group of compounds described in UK Specification No. 2152049 may be represented by the general formula (IX):

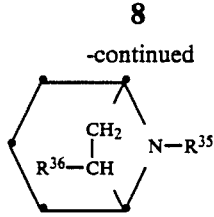 (IX)

wherein R$^1$, R$^2$ and R$^3$ are as defined for general formula (I) and G is a group of formula (d) or (e):

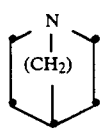 (d)

-continued

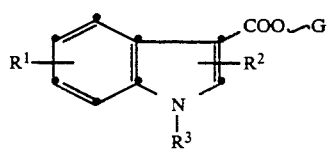 (e)

wherein R$^{35}$ is C$_{1-4}$ alkyl and R$^{36}$ is methoxy;
and pharmaceutically acceptable salts thereof.

Particularly preferred compounds for use according to the present invention are (3α-tropanyl)-1H-indole-3-carboxylic acid ester and endo-N-(9-methyl-9-azabicyclo[3,3,1]non-3-yl)-1-methylindazole-3-carboxamide.

Other preferred compounds for use according to the present invention are: 3-(5-methyl-1H-imidazol-4-yl)-1-(1-methyl-1H-indol-3-yl)-1-propanone; 1αH, 3αH-tropan-3-yl-3,5-dimethylbenzoate; and (±)-endo-4-amino-5-chloro-2-methoxy-N-(1-azabiyclo)-[3.3.1]-non-4-yl)benzamide, particularly in the form of its hydrochloride hydrate.

Further preferred compounds for use according to the present invention are: 1αH,3α,5αH-tropan-3-yl-3,5-dichlorobenzoate; indole-[5-(2-methyl-2-azabicyclo(2.2.2)octyl]-3-carboxylate; 1H-indol-3-yl-carboxylic acid (3R*,4S*)-1-azabicyclo-[2.2.1]hept-3-yl ester; 1H-indolyl-3-carboxylic acid 2S-(1-methyl-2-pyrrolidinylmethyl) ester; 4-amino-5-chloro-2-methoxy-N-(3-quinuclidinylmethyl)benzamide; 1-methyl-3-indazolecarboxylic acid (endo-8-methyl-8-azabicyclo [3,2,1]oct-3-yl)ester; (±)4-amino-5-chloro-2-methoxy-N-(6'α-[4'-thia-1'-azabicyclo[3,3,1]nonyl])benzamide; (±)4-amino-5-chloro-2-methoxy-N-(6'α-[4'-oxa-1'-azabicyclo[3,3,1]nonyl])benzamide; and physiologically acceptable salts and solvates thereof.

The invention also provides a pharmaceutical composition which comprises an effective amount of at least one compound (e.g. an azabicyclo derivative or a benzoic acid derivative) which acts as an antagonist of 5-HT at 5-HT$_3$ receptors, for use in human or veterinary medicine, for the relief or prevention of a withdrawal syndrome resulting from addiction to a drug or substance of abuse and/or for the suppression of dependence on drugs or substances of abuse.

In a further aspect the invention provides for the use of a compound (e.g. an azabicyclo derivative or a benzoic acid derivative) which acts as an antagonist of 5-HT at 5-HT$_3$ receptors for the manufacture of a medicament for the relief or prevention of a withdrawal syndrome resulting from addiction to a drug or substance of abuse and/or for the suppression of dependence on drugs or substances of abuse.

Pharmaceutical compositions for use according to the present invention may be formulated in conventional manner, optionally with one or more physiologically acceptable carriers and/or excipients. For example, the compounds described in the aforementioned patent specifications may be formulated in the manner described therein.

Compounds for use according to the present invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

Compounds for use according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds for use according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds for use according to the present invention may be formulated with suitable polymeric or hydrophobic materials (for example as an emulsion in an acceptable oil) or ion exchange resins, or as sparingly soluble derivatives, for example, as a sparingly soluble salt.

The dose at which the compounds may be administered to man will depend upon the route of administration, the body weight of the patient, the severity of the condition to be treated and the potency of the compounds. For example, the compounds disclosed in the aforementioned patent specifications may be administered at doses in the ranges specified therein for the compounds, or at lower doses for example 0.5 $\mu$g to 20 mg e.g. 0.005–20 mg, preferably 0.05–10 mg per unit dose which may be administered, for example, 1 to 4 times per day.

Thus a unit dose of a compound of formula (I) as herein defined may contain from 0.2 to 250 mg of the active ingredient, and may be administered for example up to four times per day, such that the overall daily dose is in the range 0.5 to 500 mg.

A unit dose of a compound of formula (II) as herein defined may contain from about 0.5 to 100 mg of the active ingredient, usually 1 to 50 mg and preferably 3 to 30 mg, and may be administered, for example, from 1 to 4 times per day.

A unit dose of a compound of formula (III) as herein defined may contain 0.1 to 20 mg of the active ingredient, for example 0.5 to 10 mg, and may be administered, for example, up to six times per day, such that the total daily dose is normally in the range 0.01 to 10 mg/kg.

A unit dose of a compound of formula (IV) as herein defined may contain 0.5 to 100 mg of the active ingredient, for example 1 to 500 mg, and may be administered, for example, 1 to 4 times per day, such that the total daily dose is in the range 0.001 to 50 mg/kg, more usually 0.002 to 25 mg/kg.

A unit dose of a compound of formula (V) as herein defined may contain 0.05 to 20 mg of the active ingredient, preferably 0.1 to 10 mg, and may be administered 1 to 4 times per day.

A unit dose of a compound of formula (VI) as herein defined may contain 0.001 to 100 mg of the active ingredient, preferably 0.01 to 50 mg, and may be administered 1 to 4 times per day.

A unit dose of a compound of formula (VII) as herein defined may contain 0.05 to 1000 mg of the active ingredient, for example 0.1 to 500 mg, and may be administered, for example, 1 to 4 times per day, such that the total daily dose is in the range 0.0001 to 50 mg/kg, more usually 0.0002 to 25 mg/kg.

A unit dose of a compound of formula (VIII) as herein defined may contain 0.05 to 1000 mg of the active ingredient, for example 0.5 to 500 mg, and may be administered, for example, 1 to 4 times per day, such that the total daily dose is in the range 0.0001 to 50 mg/kg, more usually 0.0002 to 25 mg/kg.

A unit dose of a compound of formula (IX) as herein defined may contain from 0.1 to 250 mg of the active ingredient, and may be administered up to four times per day, such that the overall daily dose is in the range 0.5 to 500 mg.

The following examples illustrate pharmaceutical formulations for use according to the invention, containing either (3$\alpha$-tropanyl)-1H-indole-3-carboxylic acid ester or a compound of formula (VI) as the active ingredient.

Other compounds which are antagonists of 5-HT at 5-HT$_3$ receptors may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Direct Compression

| Tablet | mg/tablet |
| --- | --- |
| Active Ingredient | 0.50 |
| Calcium Hydrogen Phosphate BP* | 87.25 |

| -continued | |
|---|---|
| Tablet | mg/tablet |
| Croscarmellose Sodium NF | 1.8 |
| Magnesium Stearate BP | 0.45 |
| Compression weight | 90.0 |

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

Tablets of other strengths may be prepared by altering the ratio of active ingredient to excipients or the compression weight and using punches to suit.

CAPSULES

| | mg/tablet |
|---|---|
| Active Ingredient | 0.5 |
| *Starch 1500 | 98.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

This may be either a sucrose or sucrose free presentation.

| Sucrose-Free | mg/5 ml dose |
|---|---|
| Active ingredient | 0.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

Injection for Intravenous Administration

| | mg/ml | |
|---|---|---|
| Active ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

SUPPOSITORY

| Active Ingredient | 0.5 mg |
|---|---|
| *Witepsol H15 to | 1.0 g |

*Witepsol H15 is a propreitary grade of Adeps Solidus Ph. Eur.

A suspension of the active ingredient is prepared in the molten Witepsol and filled, using suitable machinery, into 1 g size suppository moulds.

The efficacy of the compounds for use according to the present invention in the treatment of a withdrawal syndrome after addiction to a drug or substance of abuse has been demonstrated in animals using, for example, the light/dark exploration test in mice.

Test Compound Y: 3-(5-methyl-1H-imidazol-4-yl)-1-(1-methyl-1H-indol-3-yl)-1-propanone.

Test Compound Z: (3α-tropanyl)-1H-indole-3-carboxylic acid ester.

Light/Dark Exploration Test in Mice

Animals

Male albino BKW mice, 25–30 g, were housed 10 to a cage and allowed free access to food and water. They were kept on a reversed light cycle with the lights on between 22.00 h and 10.00 h.

Procedure and Results

The method was based on that described by J. Crawley and F. K. Goodwin, Pharmacol. Biochem. and Behaviours, 1980, 13, 167–170.

The apparatus was an open-topped box, 45 cm long, 27 cm wide and 27 cm high, divided into a small (2/5) area and a large (3/5) area by a partition that extended 20 cm above the walls. There was a 7.5×7.5 cm opening in the partition at floor level. The small compartment was painted black and the large compartment white. The floor of each compartment was marked into 9 cm squares. The white compartment was illuminated by a 100 W tungsten bulb 17 cm above the box and the black compartment by a similarly placed 60 W red bulb. The laboratory was illuminated with red light.

All tests were performed between 13.00 h and 18.00 h. Each mouse was tested by placing it in the centre of the white area and allowing it to explore the novel environment for 5 minutes. Its behaviour was recorded on videotape and the behavioural analysis was performed subsequently from the recording. Five parameters were measured: the latency to entry into the dark compartments, the time spent in each area, the number of transitions between compartment, the number of lines crossed in each compartment and the number of times the mice stood up on their hind legs only (i.e. the number of rears) in each compartment. Drugs were administered intraperitoneally except where otherwise stated.

Thus, in Experiments 1 and 2 groups of mice (5 per group) were treated with alcohol (8% v/v in drinking water) for 14 days, and then either:

(A): the alcohol dosing was abruptly ceased and the mice were tested 2½ days after the last dose;

or (B): as (A) with administration of the test compound Y, 10 ng/kg (Experiment 1) or the test compound Z, 0.01 mg/kg (Experiment 2), on 5 separate occasions over the 2½ day alcohol withdrawal period.

| Treatment | Rears/5 min (light) | Rears/5 min (dark) |
|---|---|---|
| Experiment 1 | | |
| Vehicle | 26.0 | 39.0 |
| (A) Alcohol withdrawal | 9.0[1] | 62.0[1] |
| (B) Alcohol withdrawal + Test compound Y (10 ng/kg) | 44.0[1,2] | 32.0[1,2] |
| Experiment 2 | | |
| Vehicle | 16.7 | 29.3 |
| (A) Alcohol withdrawal | 8.7[1] | 44.7[1] |
| (B) Alcohol withdrawal + Test Compound Z (0.01 mg/kg) | 14.7 | 44.0[1] |

Results are means, standard error of the mean less than 11.7%.
1 $p<0.01$ vs vehicle control
2 $p<0.01$ vs alcohol withdrawal
Dunnett's t-test.

Conclusions

In test (A) of both Experiments 1 and 2, the mice displayed an abstinence syndrome manifest as an increased tendency to stay in the dark area. Administration of either test compound resulted in the prevention or reversal of this abstinence syndrome.

I claim:

1. A method of treatment for the relief or prevention of a withdrawal syndrome resulting from addiction to a drug and/or for the suppression of dependence on drugs, which comprises administering to a human or animal subject suffering from or liable to suffer from said withdrawal syndrome and/or dependent on a drug an effective amount of a compound of formula (IV):

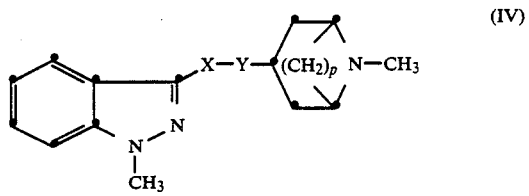

wherein X is CO and Y is NH or O;
and p is 2 or 3;
or a pharmaceutically acceptable salt thereof.

2. A method according to claim 1 wherein the compound of formula (IV) is endo-N-(9-methyl-9-azabicyclo[3,3,1]non-3-yl)-1-methyl-indazole-3-carboxamide.

3. A method according to claim 1 wherein said compound of formula (IV) or a pharmaceutically acceptable salt thereof is administered in a dose of 0.5 μg to 20 mg from 1 to 4 times per day.

4. A method according to claim 3 wherein said dose is from 0.05 mg to 10 mg from 1 to 4 times per day.

5. A method according to claim 1 wherein said compound of formula (IV) is administered orally, buccally, parenterally, rectally or as a depot preparation.

6. A method according to claim 1 wherein said drug is an opiate.

7. A method according to claim 1 wherein said drug is cocaine.

8. A method according to claim 1 wherein said drug is a benzodiazepine.

* * * * *